(12) United States Patent
Dalko et al.

(10) Patent No.: US 7,598,278 B2
(45) Date of Patent: Oct. 6, 2009

(54) ADMINISTRATION OF PYRIDINEDICARBOXYLIC ACID COMPOUNDS FOR STIMULATING OR INDUCING THE GROWTH OF HUMAN KERATINOUS FIBERS AND/OR ARRESTING THEIR LOSS

(75) Inventors: Mario Dalko, S/Yvette (FR); Geneviéve Loussouarn, Clichy (FR); Charles El Rawadi, Rueil-Malmaison (FR); Christophe Boulle, Lagny-sur-Marne (FR); Bruno Bernard, Neuill-sur-Seine (FR)

(73) Assignee: L'Oreal, Paris (FR)

( * ) Notice: Subject to any disclaimer, the term of this patent is extended or adjusted under 35 U.S.C. 154(b) by 503 days.

(21) Appl. No.: 10/410,402

(22) Filed: Apr. 10, 2003

(65) Prior Publication Data

US 2003/0223945 A1 Dec. 4, 2003

Related U.S. Application Data

(60) Provisional application No. 60/372,414, filed on Apr. 16, 2002.

(30) Foreign Application Priority Data

Apr. 11, 2002 (FR) .................................. 02 04527

(51) Int. Cl.
*A61K 31/44* (2006.01)
(52) U.S. Cl. .......................................... 514/354; 424/59
(58) Field of Classification Search ...................... 514/1, 514/356, 354
See application file for complete search history.

(56) References Cited

U.S. PATENT DOCUMENTS

| | | | | |
|---|---|---|---|---|
| 5,472,617 A | * | 12/1995 | Barthold et al. | ............. 210/708 |
| 5,472,687 A | | 12/1995 | Proctor | |
| 5,582,817 A | * | 12/1996 | Otsu et al. | ..................... 424/59 |
| 5,786,379 A | | 7/1998 | Bernardon | |
| 6,020,139 A | | 2/2000 | Schwartz et al. | |

FOREIGN PATENT DOCUMENTS

| | | |
|---|---|---|
| EP | 0 176 741 A1 | 8/1984 |
| EP | 0 433 457 A1 | 12/1990 |
| EP | 583479 | 3/1993 |
| EP | 0 583 479 A1 | 2/1994 |
| FR | 2159400 | 6/1973 |
| FR | 2 677 247 A1 | 12/1992 |
| FR | 2733053 | 12/1997 |
| GB | 1408036 | 10/1975 |
| JP | 01-301612 | 12/1989 |
| JP | 03-287536 | 12/1991 |
| JP | 2001-253808 | 9/2001 |
| JP | 2001-288048 | 10/2001 |
| JP | 2002-80327 | 3/2002 |
| WO | WO 98/55091 A1 | 12/1998 |
| WO | WO 99/62881 A1 | 12/1998 |
| WO | WO 99/62483 A1 | 12/1999 |

OTHER PUBLICATIONS

Akira, "Hair Growth Agent", Patent Abstract of Japan, Publication No. 01301612, Publication Date—Dec. 5, 1989, Application No. 62010066.

* cited by examiner

*Primary Examiner*—Ardin Marschel
*Assistant Examiner*—James D Anderson
(74) *Attorney, Agent, or Firm*—Buchanan, Ingersoll & Rooney P.C.

(57) ABSTRACT

The invention relates to the use in a composition for caring for human hair or eyelashes of an effective amount of a pyridinedicarboxylic acid derivative of general formula (I) or of one of its salts,

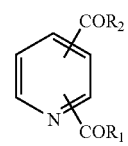

(I)

in which $R_1$ and $R_2$ represent, independently of one another, OH, OR', —$NH_2$, —NHR' or —NR'R", and R' and R" represent, independently of one another, a saturated or unsaturated and linear or branched $C_1$-$C_{18}$ alkyl radical or an aryl radical, this alkyl or aryl radical optionally being substituted by at least one OH, alkoxy, acyloxy, amino or alkylamino group, or R' and R" together represent a heterocycle, the composition being intended to induce and/or stimulate the growth of human keratinous fibers, such as the hair and eyelashes, and/or slow down their loss; the invention also relates to a cosmetic treatment intended to stimulate the growth of human keratinous fibers, such as the hair and eyelashes, and/or slow down their loss.

4 Claims, No Drawings

ADMINISTRATION OF PYRIDINEDICARBOXYLIC ACID COMPOUNDS FOR STIMULATING OR INDUCING THE GROWTH OF HUMAN KERATINOUS FIBERS AND/OR ARRESTING THEIR LOSS

CROSS-REFERENCE TO PRIORITY/PROVISIONAL APPLICATIONS

This application claims priority under 35 U.S.C. §119 of FR-02/04527, filed Apr. 11, 2002, and of provisional application Ser. No. 60/372,414, filed Apr. 16, 2002, both hereby expressly incorporated by reference. This application is also a continuation of said '414 provisional.

BACKGROUND OF THE INVENTION

1. Technical Field of the Invention

A subject-matter of the invention is the use of an effective amount of a pyridinedicarboxylic acid derivative or of one of its salts in a composition intended to induce and/or stimulate the growth of human keratinous fibers and in particular of human hair and eyelashes and/or to slow down their loss. In addition, it relates to a cosmetic treatment process intended to stimulate the growth of human keratinous fibers, such as the hair and eyelashes, and/or to retard their loss.

2. Description of the Prior Art

Hair growth and its replacement are mainly determined by the activity of the hair follicles and their matrix environment. Their activity is cyclical and comprises essentially three phases, namely the anagenic phase, the catagenic phase and the telogenic phase.

The anagenic phase (active or growth phase), which lasts several years and during which the hair grows longer, is followed by a very short and transitory catagenic phase, which lasts a few weeks, and then by a telogenic phase or resting phase, which lasts a few months.

At the end of the resting period, the hair falls out and another cycle recommences. The head of hair is thus constantly replaced and, of the approximately 150,000 hairs which a head of hair comprises, approximately 10% are at rest and will be replaced in the months to come.

Natural hair loss can be estimated, on average, at a few hundred individual hairs per day for a normal physiological state. This process of constant physical replacement undergoes a natural change with aging, the hair becomes finer and its cycles shorter.

In addition, various causes can result in significant hair loss, whether temporary or definitive. Hair loss, in particular alopecia, is essentially due to disturbances in hair replacement. These disturbances result first in the acceleration in the frequency of the cycles, at the expense of the quality of the hair and then of their quantity. The bulbs gradually become smaller and, at the same time, the latter become isolated by gradual thickening of the perifollicular collagen matrix and of the external connective tissue sheath. Revascularization about the hair follicle is therefore rendered more difficult cycle after cycle. Individual hairs regress, becoming smaller until no more than an unpigmented down, and this phenomenon results in a gradual thinning of the head of hair.

Areas are preferentially affected, in particular the temporal or frontal regions in men and, in women, diffuse alopecia of the vertex is observed.

The term "alopecia" also covers a whole family of conditions of the hair follicle having, as final consequence, the definitive loss, partial or general, of the hair. It relates more particularly to androgenic alopecia. In a large number of cases, early hair loss occurs in genetically predisposed individuals. This is then androchronogenetic alopecia; this form of alopecia concerns men in particular.

Furthermore, it is known that certain factors, such as a hormone imbalance, a physiological stress or malnutrition, can accentuate the phenomenon. In addition, hair loss or detrimental change can be related to seasonal phenomena.

Generally, any factor which influences these processes, namely the acceleration in the frequency of the cycles, the gradual reduction in size of the bulbs, the gradual thickening of the perifollicular collagen matrix, the thickening of the external connective tissue sheath and the reduction in vascularization, will have an effect on the growth of the hair follicles.

SUMMARY OF THE INVENTION

It has now unexpectedly been found that pyridinedicarboxylic acids and certain derivatives of these pyridinedicarboxylic acids, in particular esters and amides, surprisingly possess a favorable activity in maintaining and/or improving the density of human keratinous fibers and in particular the hair density in man and/or reducing the variation in the diameters of keratinous fibers and more especially of head hairs in man. Increasing the density of keratinous fibers, in particular hair fibers, is understood to mean increasing the number of keratinous fibers, in particular of head hairs, per $cm^2$ of skin and in particular of scalp.

The present invention therefore features the use of at least one pyridinedicarboxylic acid derivative of general formula (I) or of one of its salts

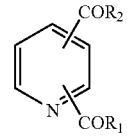

in which $R_1$ and $R_2$ represent, independently of one another, OH, OR', —$NH_2$, —NHR' or —NR'R", and R' and R" represent, independently of one another, a saturated or unsaturated and linear or branched $C_1$-$C_{18}$ alkyl radical or an aryl radical, this alkyl or aryl radical optionally being substituted by at least one OH, alkoxy, acyloxy, amino or alkylamino group, or R' and R" together represent a heterocycle, in a cosmetic composition for caring for and/or making up keratinous fibers or for the preparation of a composition for caring for and/or treating keratinous fibers, to or intended to induce and/or stimulate the growth of human keratinous fibers and/or slow down their loss and/or increase their density.

This invention also features a cosmetic regime or regimen comprising administering at least one pyridinedicarboxylic acid derivative of formula (I) or one of its salts as defined above in a cosmetic composition as agent for inducing and/or stimulating the growth of human keratinous fibers and/or slowing down their loss and/or increasing their density.

The human keratinous fibers to which the invention applies are in particular the hair, eyebrows, eyelashes, beard hairs, moustache hairs and pubic hairs. More particularly, the invention applies to human hair and/or eyelashes.

Consequently, the invention also relates to the cosmetic use of at least one pyridinedicarboxylic acid derivative of formula (I) or of one of its salts in a cosmetic composition for human hair care, for treating androgenic alopecia, and to the use of at least one pyridinedicarboxylic acid derivative of formula (I) or of one of its salts for the preparation of a composition for human hair care intended to treat androgenic alopecia. Thus, this composition makes it possible to keep the head of hair in good condition and/or to combat natural hair loss in men.

A further subject-matter of the invention is the cosmetic use of at least one pyridinedicarboxylic acid derivative of formula (I) or of one of its salts as defined above in a cosmetic composition for caring for and/or making up human eyelashes or for the preparation of a composition for caring for and/or treating human eyelashes, to or intended to induce and/or stimulate the growth of the eyelashes and/or increase their density. This composition thus makes it possible to keep the eyelashes in good condition and/or to improve their condition and/or their appearance.

DETAILED DESCRIPTION OF BEST MODE AND SPECIFIC/PREFERRED EMBODIMENTS OF THE INVENTION

According to the invention, "at least one" derivative means one or more (2, 3 or more) derivatives.

The derivatives to which the invention applies are known as such; they can be manufactured in a known way.

Thus, pyridine-2,4-dicarboxylic and pyridine-2,5-dicarboxylic acids have been described as very weak inhibitors of proline hydroxylase (K. Majamaa et al., Eur. J. Biochem., 138, 1984, 239-245). Sharir et al. have suggested the use of pyridine-2,4-dicarboxylic acid to slow down the healing of a surgical wound (Current Eye Research, vol. 12(6), 1993, 15 553-559).

U.S. Pat. No. 4,717,727 teaches that esters of pyridine-2,4-dicarboxylic and pyridine-2,5-dicarboxylic acids can be used in the treatment of pathologies related to collagen metabolism, on the one hand, and as immunosuppressant, on the other hand.

To the knowledge of the assignee hereof, the prior art does not teach or suggest that the pyridinedicarboxylic acid derivatives or one of their salts targeted by the present invention have the property of inducing and/or stimulating the growth of human keratinous fibers and in particular of human hair and of the eyelashes and/or of slowing down their loss and/or of increasing their density.

The $C_1$-$C_{18}$ alkyl radical is preferably a saturated or unsaturated alkyl comprising from 1 to 10 carbon atoms, such as methyl, ethyl, tert-butyl, isopropyl, hexyl and others. The alkyl can comprise at least one carbon-carbon double bond or one carbon-carbon triple bond, such as, for example, —CH=CH$_2$, —CH$_2$—CH=CH—CH$_3$ or —CH$_2$—C≡CH.

According to the present invention, the term "alkoxy" is understood to mean an —O—R group in which R is a $C_1$-$C_{18}$ alkyl group as defined above. The term "acyloxy" is understood to mean an —O—CO—R group in which R is a $C_1$-$C_{18}$ alkyl group as defined above. The term "alkylamino" is understood to mean an —NH—R group in which R is a $C_1$-$C_{18}$ alkyl group as defined above.

The aryl radical can represent the phenyl or naphthyl radical.

When R' and R" together represent the heterocycle, they can represent a ring with 4 to 7 atoms and better still with 5 to 6 atoms, comprising from 1 to 4 heteroatoms chosen from O, S or N, it being possible for this ring to be saturated or unsaturated. Mention may be made, as heterocycle, of the piperidine, morpholine, imidazole, pyrazole, piperazine, pyrrolidine or thiazolidine rings.

In particular, R' and R" represent a $C_1$-$C_{18}$ and better still $C_1$-$C_{10}$ alkyl radical optionally substituted by an alkoxy or acyloxy group.

$R_1$ and $R_2$ preferably represent, independently of one another, OH, OCH$_3$, OCH$_2$—CH$_3$,

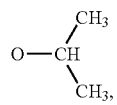

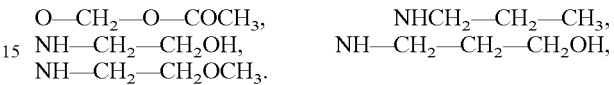

NH—CH$_2$—CH$_2$OCH$_3$.

COR$_1$ and COR$_2$ are preferably respectively in the 2 and 3 or 2 and 4 positions of the pyridine ring. However, they can be respectively in the 2 and 5 positions.

According to a preferred embodiment of the invention, the following pyridinedicarboxylic acid derivatives are used:
pyridine-2,4-dicarboxylic acid or its zinc or sodium salt,
pyridine-2,3-dicarboxylic acid or its zinc or sodium salt,
dimethyl pyridine-2,4-dicarboxylate,
dimethyl pyridine-2,3-dicarboxylate,
diethyl pyridine-2,4-dicarboxylate,
diethyl pyridine-2,3-dicarboxylate,
diethyl pyridine-2,5-dicarboxylate,
dimethyl pyridine-2,5-dicarboxylate,
diisopropyl pyridine-2,4-dicarboxylate,
2,4-di(n-propylamido) pyridine, (derivative of formula (I) with $R_1$=$R_2$=NH—(CH$_2$)$_2$—CH$_3$),
di(acetyloxymethyl) pyridine-2,4-dicarboxylate (derivative of formula (I) such that $R_1$ and $R_2$ represent O—CH$_2$—O—COCH$_3$),
2,4-di(2-hydroxyethylamido)pyridine,
2,4-di(3-hydroxypropylamido)pyridine.

Use is advantageously made of esters of pyridinedicarboxylic acid, as they have a better cutaneous penetration, and in particular diethyl pyridine-2,4-dicarboxylate.

Salts of compounds of formula (I) is understood to mean, according to the invention, the organic or inorganic salts of a compound of formula (I), said salts being physiologically acceptable.

Mention may be made, as inorganic salts which may be used according to the invention, of double sodium or potassium salts and zinc ($Zn^{2+}$), calcium ($Ca^{2+}$), copper ($Cu^{2+}$), iron ($Fe^{2+}$), strontium ($Sr^{2+}$), magnesium ($Mg^{2+}$) or manganese ($Mn^{2+}$) salts; hydroxides, carbonates or chlorides.

The organic salts which can be used according to the invention are, for example, triethanolamine, monoethanolamine, diethanolamine, hexadecylamine, N,N,N',N'-tetrakis(2-hydroxypropyl)ethylenediamine or tris(hydroxymethyl)aminomethane salts.

It is thus understood that, in the text, unless otherwise indicated, the use of the term compound of formula (I) should be understood as meaning the compound of formula (I) in the salified or nonsalified form.

The effective amount of a compound of formula (I) or of one of its salts corresponds, of course, to the amount necessary to produce the desired result (namely, to increase the density of keratinous fibers and in particular the head hairs or to promote their growth). A person skilled in the art is therefore in a position to evaluate this effective amount, which depends on the nature of the compound used and on the person to which it is applied.

To give an order of magnitude, according to the invention, the compound of formula (I) or one of its salts can be used in an amount representing from $10^{-3}$% to 10% of the total weight of the composition and preferably in an amount representing from $10^{-2}$% to 5% of the total weight of the composition, for example from 0.5% to 2%.

Also, the composition must comprise a nontoxic physiologically acceptable medium capable of being applied to the skin, including the scalp and eyelids, or to the keratinous fibers of human beings. The term "cosmetic" is understood to mean, within the meaning of the invention, a composition with a pleasant appearance, pleasant smell and pleasant feel.

The composition according to the invention can be for cosmetic or pharmaceutical use. Preferably, the composition according to the invention is for cosmetic use. The compound of formula (I) or one of its salts can be used in a composition which has to be ingested, injected or applied to the skin or keratinous fibers (over any cutaneous area of the body and fibers to be treated).

According to the invention, the compound of formula (I) or one of its salts can be used via the oral route in an amount of 0.1 to 300 mg per day, for example of 5 to 10 mg/d.

A preferred composition of the invention is a composition for cosmetic use for topical application to the skin and keratinous fibers and more particularly to the scalp, hair and eyelashes.

Depending on the method of application, this composition can be provided in any pharmaceutical dosage form normally used in the cosmetic and pharmaceutical fields.

For topical application to the skin, including the scalp, the composition can have the form in particular of an aqueous, alcoholic or aqueous/alcoholic solution or suspension, of an oily suspension or solution, of an emulsion or dispersion with a liquid or semi-liquid consistency obtained by dispersion of a fatty phase in an aqueous phase (O/W) or vice versa (W/O), of a dispersion or emulsion with a soft consistency, of an aqueous or aqueous/alcoholic or oily (anhydrous) gel, of a free or compact powder to be used as is or to be incorporated in a physiologically acceptable medium (excipient), or also of microcapsules or microparticles, or of vesicular dispersions of ionic and/or nonionic type.

It is also possible to envisage a composition in the form of a foam or alternatively in the form of an aerosol composition also comprising a pressurized propellant.

In particular, the composition for application to the scalp or hair can be provided in the form of a hair care lotion, for example for daily or twice-weekly application, of a shampoo or of a hair conditioner, in particular for twice-weekly or weekly application, of a liquid or solid soap for cleaning the scalp for daily application, of a product for shaping the hairstyle (lacquer, hairsetting product, styling gel), of a treatment mask, of a cream or of a foaming gel for cleaning the hair. It can also be provided in the form of a hair dye or mascara to be applied with a brush or comb.

Furthermore, for application to the eyelashes or hairs, the composition to which the invention applies can be provided in the form of a pigmented or nonpigmented mascara, to be applied with a brush to the eyelashes or alternatively to the beard or moustache hairs.

For use by injection, the composition can be provided in the form of an aqueous lotion or of an oily suspension, for example in the serum form. For use by ingestion or the oral route, it can be provided in the form of capsules, of granules, of syrups to be taken orally or of tablets.

According to a specific embodiment, the composition to which the invention applies is provided in the form of a hair cream or lotion, of a shampoo, of a hair conditioner, of a hair mascara or of a mascara for the eyelashes.

The amounts of the various constituents of the composition according to the invention are those conventionally used in the fields under consideration. In addition, this composition is prepared according to conventional methods. It can thus be provided in the form of a lotion, serum, milk, O/W or W/O cream, gel, ointment, pomade, powder, balm, patch, impregnated pad, soap, bar or foam.

When the composition is an emulsion, the proportion of the fatty phase can range from 2% to 80% by weight and preferably from 5% to 50% by weight with respect to the total weight of the composition.

The aqueous phase is adjusted according to the content of fatty phase and of compound(s) (I) and according to the content of possible additional ingredients, in order to obtain 100% by weight. In practice, the aqueous phase represents from 5% to 99.9% by weight.

The fatty phase can comprise fatty or oily compounds which are liquid at ambient temperature (25° C.) and atmospheric pressure (760 mmHg), generally known as oils. These oils may or may not be compatible with one another and may form a macroscopically homogeneous liquid fatty phase or a two- or three-phase system.

The fatty phase can, in addition to the oils, comprise waxes, gums, lipophilic polymers, or "pasty" or viscous products comprising solid parts and liquid parts.

The aqueous phase comprises water and optionally an ingredient miscible in any proportion with water, such as lower $C_1$ to $C_8$ alcohols, for example ethanol or isopropanol, polyols, such as propylene glycol, glycerol or sorbitol, or else acetone or ether.

The emulsifiers and coemulsifiers used in the composition in the form of an emulsion are chosen from those conventionally used in the cosmetic or pharmaceutical field. The emulsifier and the co-emulsifier are present in the composition in a proportion ranging from 0.1% to 30% by weight and preferably from 0.5% to 20% by weight with respect to the total weight of the composition and better still from 1% to 8%. In addition, their nature depends on the sense of the emulsion. In addition, the emulsion can comprise lipid vesicles and in particular liposomes.

When the composition is an oily solution or gel, the fatty phase can represent more than 90% of the total weight of the composition.

Advantageously, for a hair application, the composition is an aqueous, alcoholic or aqueous/alcoholic solution or suspension and better still a water/ethanol solution or suspension. The alcohol fraction can represent from 5% to 99.9% and better still from 8% to 80%.

For a mascara application, the composition is a wax-in-water or wax-in-oil dispersion, a gelled oil or an aqueous gel, with or without pigment.

The composition to which the invention applies can also comprise adjuvants usual in the cosmetic or pharmaceutical field chosen from hydrophilic or lipophilic gelling agents or thickeners, hydrophilic or lipophilic additives, preservatives, antioxidants (carotenoids), solvents, fragrances, fillers, odor absorbers, electrolytes, neutralizing agents, UV blocking agents, such as sunscreens, film-forming polymers, cosmetic and pharmaceutical active principles with a beneficial effect on the skin or keratinous fibers (such as vitamins) and coloring materials, which may or may not be soluble in the medium. The amounts of these various adjuvants are those conventionally used in the cosmetic field, for example from 0.01% to 20% and better still from 0.1% to 10% of the total weight of the composition. These adjuvants, depending on their nature, can be introduced into the fatty phase, into the aqueous phase and/or into the lipid vesicles and in particular liposomes.

Mention may be made, as oils or waxes which can be used in the invention, of mineral oils (liquid petrolatum, hydrogenated isoparaffin), vegetable oils (liquid fraction of karite butter, sunflower oil, soybean oil, wheat germ oil), animal oils (perhydrosqualene), synthetic oils (purcellin oil, fatty acid esters), silicone oils or waxes (linear or cyclic polydimethylsiloxanes, cyclomethicone, phenyl trimethicone), fluorinated oils (perfluoropolyethers), beeswax, candelilla wax, rice wax, carnauba wax, paraffin wax or polyethylene wax. Fatty alcohols and fatty acids (stearic acid, linoleic acid, linolenic acid) can be added to these oils and waxes.

Mention may be made, as emulsifiers which can be used in the invention, of, for example, glyceryl stearate or laurate, polyoxyethylenated sorbitol stearate or oleate (for example, polysorbate 60 and the PEG-6/PEG-32/glycol stearate mixture sold under the name of Tefose® 63 by Gattefosse) or (alkyl) dimethicone copolyols.

Mention may be made, as solvents which can be used in the invention, of lower alcohols, in particular ethanol and isopropanol, propylene glycol or certain light cosmetic oils.

Mention may be made, as hydrophilic gelling agents which can be used in the invention, of carboxy-vinyl polymers (carbomer), acrylic copolymers, such as acrylate/alkyl acrylate copolymers, polyacrylamides, polysaccharides, such as hydroxypropylcellulose, clays and natural gums and mention may be made, as lipophilic gelling agents, of modified clays, such as bentones, metal salts of fatty acids, such as aluminum stearates, hydrophobic treated silica, ethylcellulose and their mixtures.

The composition can comprise other active principles than those of formula (I) which can be hydrophilic, such as proteins or protein hydrolysates, amino acids, polyols, urea, allantoin, sugars and sugar derivatives, water-soluble vitamins, or plant extracts (of Iridaceae or of soya), it then being possible for these extracts to comprise or not to comprise isoflavones; or lipophilic, such as retinol (vitamin A) and its derivatives, in particular ester (palmitate), tocopherol (vitamin E) and its derivatives, in particular ester (acetate, palmitate), essential fatty acids, such as eicosatetraenoic acid and eicosatrienoic acid or their esters and amides, ceramides, essential oils, esters of hydroxy acids, or phospholipids, such as lecithin; or soluble in alcoholic solvents, such as lactones (kawain); or their mixtures.

According to the invention, it is possible, inter alia, to combine the compound of formula (I) or one of its salts with other additional active compounds promoting in particular the regrowth of human keratinous fibers and/or limiting their loss. These additional compounds are chosen in particular from:

- hormones, in particular of plant origin, for example estriol or its analogues, thyroxine and its salts, or progesterone;
- antibacterial agents, such as macrolides, pyranosides and tetracyclines and in particular erythromycin;
- calcium antagonist agents, such as cinnarizine, diltiazem, nimodipine, verapamil and nifedipine;
- microorganism extracts, in particular bacterial extracts;
- agents which modulate cutaneous differentiation and/or proliferation, such as retinoic acid and its isomers, retinol and its esters, vitamin D and its derivatives, or oestrogens, such as oestradiol;
- agents which modulate bacterial adhesion to the skin and/or mucous membranes, such as honey, in particular acacia honey, and certain sugar derivatives;
- agents for combating parasites, in particular metronidazole, crotamiton or pyrethroids;
- antifungals, in particular compounds belonging to the imidazole class, such as econazole, ketoconazole or miconazole or their salts, nicotinic acid esters, including in particular tocopherol nicotinate, benzyl nicotinate and $C_1$-$C_6$ alkyl nicotinates, such as methyl nicotinate or hexyl nicotinate; polyene compounds, such as amphotericin B, compounds of the allylamine family, such as terbinafine, or alternatively octopirox, selenium derivatives or anthralin;
- antiviral agents, such as acyclovir;
- steroidal anti-inflammatory agents, such as cortico-steroids, for example hydrocortisone, betamethasone valerate or clobetasol propionate, or nonsteroidal anti-inflammatory agents, such as ibuprofen and its salts, diclofenac and its salts, acetylsalicylic acid, acetaminophen, glycyrrhetinic acid or α-bisabolol;
- anaesthetic agents, such as lidocaine hydrochloride and its derivatives;
- antipruriginous agents, such as thenaldine, trimeprazine or cyproheptadine;
- keratolytic agents, such as α- and β-hydroxy-carboxylic or β-ketocarboxylic acids, their salts, amides or esters, the lactones and their corresponding salts, and more particularly hydroxy acids, such as glycolic acid, lactic acid, salicylic acid, citric acid and generally fruit acids, or salicylic acid derivatives, such as those carrying an alkanoyl radical having from 2 to 12 carbon atoms in the 5 position of the benzene ring, such as 5-(n-octanoyl) salicylic acid;
- agents for combating free radicals, such as α-tocopherol or its esters, superoxide dismutases, certain metal chelating agents or ascorbic acid and its esters;
- antiseborrheics, such as progesterone;
- antidandruff agents, such as octopirox or zinc pyrithione;
- anti-acne agents, such as retinoic acid or benzoyl peroxide;
- vasodilators, such as pyrimidine derivatives, for example 2,4-diamino-6-piperidinopyrimidine 3-oxide or "minoxidil", disclosed in U.S. Pat. Nos. 4,139,619 and 4,596,812, or diazoxide;
- agents which reduce hair loss, such as aminexil or 6-O-[(9Z,12Z)-octadeca-9,12-dienoyl]hexapyranose;
- anti-androgen agents, such as oxendolone, spironolactone, diethylstilbestrol and flutamide;
- steroidal or nonsteroidal inhibitors of 5α-reductases, such as finasteride;
- potassium channel agonists, such as cromakalim and nicorandil;
- FP receptor (receptor to prostaglandins of type F) agonists, such as latanoprost, bimatoprost, travoprost or unoprostone;
- their mixtures.

The composition according to the invention can additionally comprise substances such as substance P, CGRP or bradykinin agonists or NO-synthase inhibitors, compounds described as being active in the treatment of sensitive skin and as exhibiting anti-irritant effects, in particular with respect to irritant compounds possibly present in the compositions.

The composition according to the invention advantageously comprises at least one additional active principle which promotes the regrowth of human keratinous fibers and/or which limits the loss chosen from aminexil, FP receptor agonists and vasodilators and more particularly chosen from aminexil, minoxidil, latanoprost and travoprost.

It is also possible to envisage that the composition comprising at least the compound of formula (I) or one of its salts is in the liposomed form, such as disclosed in particular in WO 94/22468, filed on Oct. 13, 1994 by Anti Cancer, Inc. Thus, the compound encapsulated in the liposomes can be selectively delivered in the hair follicle.

The composition according to the invention, in particular the cosmetic composition, can be applied to the alopecic areas of the scalp and hair of an individual, and optionally left in contact for several hours and optionally rinsed out.

It is possible, for example, to apply the composition comprising an effective amount of a compound of formula (I) or of one of its salts in the evening, to keep the latter in contact overnight and optionally to shampoo in the morning. These applications can be repeated daily for one or more months, according to the individuals.

Thus, another subject-matter of the present invention is a process for the cosmetic treatment of human keratinous fibers and/or of the skin whence the said fibers emerge, including the scalp, characterized in that it consists in applying, to the keratinous fibers and/or the skin whence the said fibers emerge, a cosmetic composition comprising at least one derivative of formula (I) or one of its salts, in leaving the latter in contact with the keratinous fibers and/or the skin whence the said fibers emerge and optionally in rinsing the fibers and/or the skin.

This treatment process indeed exhibits the characteristics of a cosmetic process in so far as it makes it possible to improve the attractiveness of human keratinous fibers by giving them greater vigor and improved appearance. In addition, it can be used daily for several months, without medical prescription.

More particularly, a subject-matter of the present invention is a process for the cosmetic care of human hair and/or the human scalp, for the purpose of improving their condition and/or their appearance, characterized in that it consists in applying, to the hair and/or the scalp, a cosmetic composition comprising at least one derivative of formula (I) or one of its salts, in leaving the latter in contact with the hair and/or the scalp and optionally in rinsing the hair and/or the scalp.

A further subject-matter of the invention is a process for the cosmetic care of and/or for making up human eyelashes, for the purposes of improving their condition and/or their appearance, characterized in that it consists in applying a mascara composition comprising at least one compound of formula (I) or one of its salts and in leaving this composition in contact with the eyelashes. This mascara composition can be applied alone or as a base coat of a conventional pigmented mascara and can be removed like a conventional pigmented mascara.

A further subject-matter of the invention is a composition for caring for or making up keratinous fibers comprising, in a physiologically acceptable medium, in particular a cosmetic medium, at least one derivative of formula (I) or one of its salts as defined above and at least one additional active principle which promotes the regrowth of human keratinous fibers and/or which limits the loss chosen from aminexil, FP receptor agonists and vasodilators and chosen more particularly from aminexil, minoxidil, latanoprost and travoprost.

In order to further illustrate the present invention and the advantages thereof, the following specific examples are given, it being understood that same are intended only as illustrative and in nowise limitative.

EXAMPLE 1

| Hair lotion: | | |
|---|---|---|
| Diethyl pyridine-2,4-dicarboxylate | | 0.80 g |
| Propylene glycol | | 10.00 g |
| Isopropyl alcohol | q.s. for | 100.00 g |

1 ml of this lotion is applied to the scalp at a rate of once to twice daily, the scalp being gently massaged for penetration of the active principle into the epidermis. The head of hair is subsequently dried in the open air. This lotion decreases hair loss and improves the appearance and the condition of the hair.

EXAMPLE 2

| Hair lotion: | | |
|---|---|---|
| Diethyl pyridine-2,4-dicarboxylate | | 2 g |
| Propylene glycol | | 30.00 g |
| Ethyl alcohol | | 40.00 g |
| Water | q.s. for | 100.00 g |

This lotion is applied to the scalp once to twice daily in a proportion of 1 ml per application, the scalp being gently massaged. The head of hair is subsequently dried in the open air.

EXAMPLE 3

| Hair lotion: | | |
|---|---|---|
| Diethyl pyridine-2,4-dicarboxylate | | 2 g |
| Ethyl alcohol | | 40.00 g |
| Water | q.s. for | 100.00 g |

This lotion is applied to the scalp once to twice daily in a proportion of 1 ml per application, the scalp being gently massaged. The hair is subsequently dried in the open air or using a hair dryer.

EXAMPLE 4

| Hair lotion: | | |
|---|---|---|
| Diisopropyl pyridine-2,4-dicarboxylate | | 2 g |
| Propylene glycol | | 30.00 g |
| Ethyl alcohol | | 40.00 g |
| Water | q.s. for | 100.00 g |

1 ml of this lotion is applied to the scalp at the rate of once to twice daily, the scalp being gently massaged. The hair is subsequently dried in the open air or using a hair dryer.

EXAMPLE 5

| Thickened hair lotion: | | |
|---|---|---|
| Dimethyl pyridine-2,4-dicarboxylate | | 0.50 g |
| Kawain | | 2.00 g |
| Klucel G ®* | | 3.50 g |
| Ethyl alcohol | q.s. for | 100.00 g |

This thickened lotion is applied to the scalp once to twice daily in a proportion of 1 ml per application, the scalp being gently massaged. The hair is subsequently dried in the open air or using a hair dryer.

EXAMPLE 6

| Hair lotion: | | |
|---|---|---|
| Dimethyl pyridine-2,4-dicarboxylate | | 1.00 g |
| Dowanol PM ®** | | 20.00 g |
| Klucel G ®* | | 3.00 g |
| Ethyl alcohol | | 40.00 g |
| Water | q.s. for | 100.00 g |

This thickened lotion is applied to the scalp once to twice daily in a proportion of 1 ml per application, the scalp being gently massaged. The hair is subsequently dried in the open air or using a hair dryer.

EXAMPLE 7

| Hair lotion: | | |
|---|---|---|
| Sodium salt of pyridine-2,4-dicarboxylic acid | | 5.00 g |
| Ethyl alcohol | | 20.00 g |
| Water | q.s. for | 100.00 g |

This lotion is applied to the scalp once to twice daily in a proportion of 1 ml per application.

EXAMPLE 8

| Hair lotion: | | |
|---|---|---|
| Diethyl pyridine-2,4-dicarboxylate | | 2 g |
| Ethyl alcohol | | 50.00 g |
| Aminexil | | 1.50 g |
| Water | q.s. for | 100.00 g |

This lotion is applied to the scalp once to twice daily in a proportion of 1 ml per application, the scalp being gently massaged. The hair is subsequently dried in the open air or using a hair dryer.

EXAMPLE 9

| Hair lotion: | | |
|---|---|---|
| Diethyl pyridine-2,4-dicarboxylate | | 2 g |
| Aminexil | | 1.5 g |
| Propylene glycol | | 30.00 g |
| Ethyl alcohol | | 40.00 g |
| Water | q.s. for | 100.00 g |

This lotion is applied to the scalp once to twice daily in a proportion of 1 ml per application, the scalp being gently massaged. The head of hair is subsequently dried in the open air.

EXAMPLE 10

Composition for the Oral Route:

Soft capsules having the following composition are prepared in a way conventional to a person skilled in the art:

| Hydrogenated soybean oil | 40 mg |
|---|---|
| Wheat germ oil | 95 mg |
| Soybean lecithin | 20 mg |
| Natural tocopherols | 5 mg |
| Ascorbic acid | 30 mg |
| Dimethyl pyridine-2,4-dicarboxylate | 10 mg |

This composition is used once to twice daily in a proportion of one capsule per absorption.

*: Hydroxypropylcellulose, sold by Hercules
**: Propylene glycol monomethyl ether, sold by Dow Chemical.

EXAMPLE 11

| Hair lotion: | | |
|---|---|---|
| Na salt of pyridine-2,4-dicarboxylic acid | | 2 g |
| Aminexil | | 1.5 g |
| Ethyl alcohol | | 40 g |
| Water | q.s. for | 100.00 g |

This lotion is applied to the scalp once to twice daily in a proportion of 1 ml per application, the scalp being gently massaged. The head of hair is subsequently dried in the open air.

EXAMPLE 12

| Hair lotion: | |
|---|---|
| Diethyl pyridine-2,4-dicarboxylate | 2 g |
| Latanoprost | 0.005 g |

-continued

| Hair lotion: | | |
|---|---|---|
| Propylene glycol | | 30 g |
| Ethyl alcohol | | 40 g |
| Water | q.s. for | 100.00 g |

This lotion is applied to the scalp once to twice daily in a proportion of 1 ml per application, the scalp being gently massaged. The head of hair is subsequently dried in the open air.

EXAMPLE 13

In Vivo Activity:

1st Study:

Pyridine-2,4-dicarboxylic acid was tested in vivo on 25 men exhibiting androgenetic alopecia of stage III to V according to the Hamilton classification.

It was studied at a concentration of 2%, formulated in a ternary lotion based on propylene glycol, ethanol and water.

Each volunteer was treated once daily, 5 days per week, for 3 months, an area of the scalp receiving 30 µl of the lotion comprising the active principle and another area receiving the vehicle alone (placebo).

The evaluation of the effectiveness of the treatments was carried out by determining the total pilar density of hairs per $cm^2$ (DE) using the phototrichogram technique. This examination was carried out before treatment (M0) and after 3 months of treatment (M3).

The results (mean±standard deviation) and the variations with respect to M0 are presented in the following table:

| | Placebo | | 2% Pyridine-2,4-dicarboxylic acid | |
|---|---|---|---|---|
| | No. of hairs/per $cm^2$ (DE) | DE variation (%) | No. of hairs/per $cm^2$ (DE) | DE variation (%) |
| M0 | 217 ± 50 | / | 213 ± 45 | / |
| M3 | 218 ± 57 | 0% | 224 ± 53 | 4.4% |

The results show an increase in the total density for the areas treated with pyridine-2,4-di-carboxylic acid, whereas those areas which have received the placebo do not change.

2nd Study:

Pyridine-2,4-dicarboxylic acid was tested in the form of the Na double salt formulated at a concentration of 5% in an aqueous/alcoholic lotion.

The study was carried out versus placebo on 22 men exhibiting androgenetic alopecia of stage III to V according to the Hamilton classification.

Each volunteer was treated once daily, 5 days per week, for 3 months, an area of the scalp receiving 30 µl of the lotion comprising the active principle and another area receiving the vehicle alone.

The evaluation of the effectiveness of the treatments was carried out by determining the total pilar density of hairs per $cm^2$ (DE) using the phototrichogram technique. This examination was carried out before treatment (M0) and after 3 months of treatment (M3).

The results (mean±standard deviation) and the mean of the variation with respect to M0 are presented in the following table:

| | Placebo | | 5% Na disalt of Pyridine-2,4-dicarboxylic acid | |
|---|---|---|---|---|
| | No. of hairs/per $cm^2$ (DE) | DE variation (%) | No. of hairs/per $cm^2$ (DE) | DE variation (%) |
| M0 | 247 ± 52 | / | 249 ± 50 | / |
| M3 | 236 ± 52 | −4.6% | 246 ± 50 | −0.97% |

The results show a decrease in the total density over the areas which have received the placebo. This hair loss is 4 times smaller for the areas which have received the Na double salt of pyridine-2,4-di-carboxylic acid.

The two studies, carried out in vivo on alopecic individuals, show an activity of pyridine-2,4-dicarboxylic acid and of its Na double salt, in comparison with a placebo, in favor of an increase in or a maintenance of the density of the hairs.

Each patent, patent application and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A regime or regimen for treating androgenic alopecia, comprising administering to an individual in need of such treatment, a thus effective amount of pyridine-2,4-dicarboxylic acid.

2. A regime or regimen for inducing/stimulating the growth of human keratinous fibers and/or retarding the loss and/or increasing the density thereof, comprising administering to an individual subject in need of such treatment, a thus effective amount of diethyl pyridine-2,4-dicarboxylate.

3. A regime or regimen for inducing/stimulating the growth of human head hair and/or retarding the loss and/or increasing the density thereof, comprising topically applying onto the hair and/or scalp of an individual in need of such treatment, a thus effective amount of diethyl pyridine-2, 4-dicarboxylate.

4. A regime or regimen for treating androgenic alopecia, comprising administering to an individual in need of such treatment, a thus effective amount of diethyl pyridine-2,4-dicarboxylate.

* * * * *